(12) United States Patent
Besselink et al.

(10) Patent No.: US 7,776,062 B2
(45) Date of Patent: Aug. 17, 2010

(54) SELF-ACTIVATING ENDOLUMINAL DEVICE

(76) Inventors: Petrus A. Besselink, Gronausestraat 1220, 7534 ET Enschede (NL); Hans Hanssen, Kerkdijk 44, 6577 JL Erlecom (NL); Wouter Markus, Molenheide 8, 5737 PE Lieshout (NL)

( * ) Notice: Subject to any disclaimer, the term of this patent is extended or adjusted under 35 U.S.C. 154(b) by 432 days.

(21) Appl. No.: 10/974,539

(22) Filed: Oct. 27, 2004

(65) Prior Publication Data
US 2005/0113862 A1    May 26, 2005

Related U.S. Application Data

(60) Provisional application No. 60/514,806, filed on Oct. 27, 2003.

(51) Int. Cl.
*A61M 29/00*    (2006.01)
(52) U.S. Cl. .................. 606/191; 600/184; 604/108
(58) Field of Classification Search .......... 606/200, 606/159, 191; 604/105, 528, 104, 107, 164.01, 604/106, 108, 109; 600/433–435, 184
See application file for complete search history.

(56) References Cited

U.S. PATENT DOCUMENTS

| | | | | |
|---|---|---|---|---|
| 1,870,942 | A * | 8/1932 | Beatty | 604/58 |
| 3,547,103 | A | 12/1970 | Cook | |
| 3,692,029 | A * | 9/1972 | Adair | 604/105 |
| 4,215,703 | A | 8/1980 | Willson | |
| 4,884,579 | A | 12/1989 | Engelson | |
| 5,178,158 | A * | 1/1993 | de Toledo | 600/585 |
| 5,330,497 | A * | 7/1994 | Freitas et al. | 606/185 |
| 5,397,304 | A * | 3/1995 | Truckai | 604/528 |
| 5,741,429 | A | 4/1998 | Donadio, III et al. | |
| 6,136,016 | A * | 10/2000 | Barbut et al. | 606/200 |
| 6,254,550 | B1 | 7/2001 | McNamara et al. | |
| 6,355,051 | B1 * | 3/2002 | Sisskind et al. | 606/200 |
| 6,447,485 | B2 | 9/2002 | Bierman | |
| 6,511,496 | B1 * | 1/2003 | Huter et al. | 606/200 |
| 6,544,262 | B2 | 4/2003 | Fleischman | |
| 6,595,989 | B1 | 7/2003 | Schaer | |
| 6,599,254 | B2 | 7/2003 | Winters | |
| 6,673,042 | B1 * | 1/2004 | Samson et al. | 604/104 |
| 6,755,794 | B2 | 6/2004 | Soukup | |

(Continued)

FOREIGN PATENT DOCUMENTS

WO    WO 9634560 A    11/1996

*Primary Examiner*—Anhtuan T Nguyen
*Assistant Examiner*—Ryan J Severson
(74) *Attorney, Agent, or Firm*—Dinsmore & Shohl LLP

(57) ABSTRACT

An improved endoluminal device. The device includes at least a control element (such as a guide wire) connected to a surrounding sheath and an elastic bias section to control changes to a bias force formed between the control element and the sheath. By applying an external force at a proximal end of the device, the shape can change between varying degrees of deformed shapes and an undeformed shape. In this way, both ease of insertion into the body lumen and anchoring to the lumen is promoted. A distal end of the assembly can be made to change shape for improved steerability, anchoring or both. In a particular form, the anchoring section can work as a floating parachute-like device to pull the assembly by means of the flow in the body lumen, while in a more particular form, the floating parachute-like device may be modified to act as a filter for trapping emboli.

75 Claims, 9 Drawing Sheets

U.S. PATENT DOCUMENTS 6,776,765 B2 8/2004 Soukup et al.
2002/0082585 A1* 6/2002 Carroll et al. ............... 604/528
2003/0069522 A1 4/2003 Jacobsen et al.
2004/0092845 A1 5/2004 Gaber

* cited by examiner

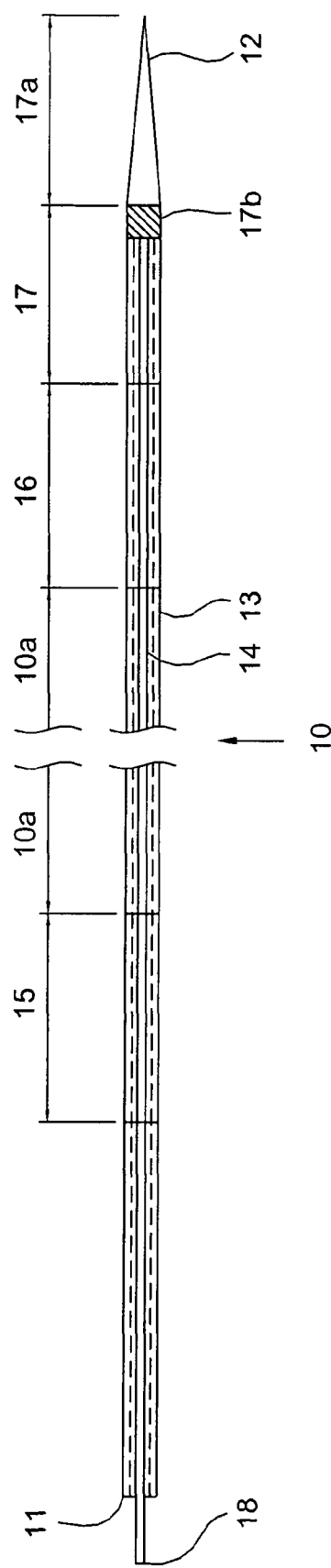
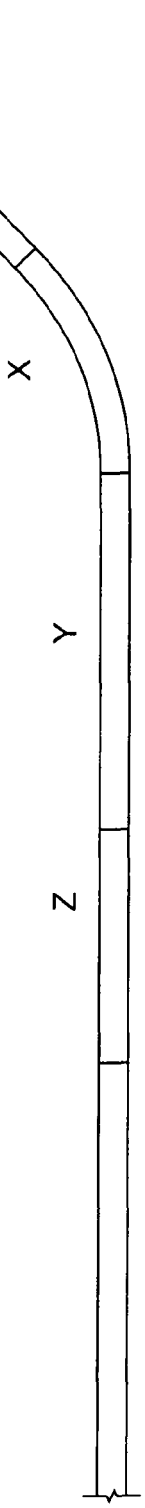
FIG. 1
FIG. 2

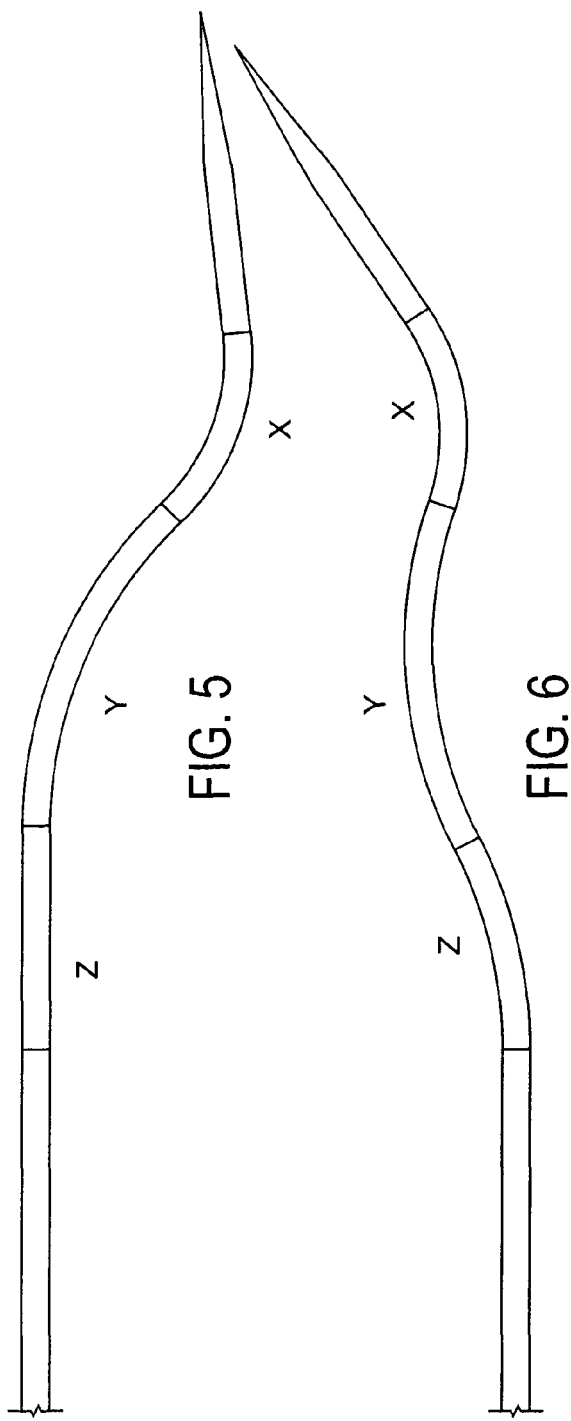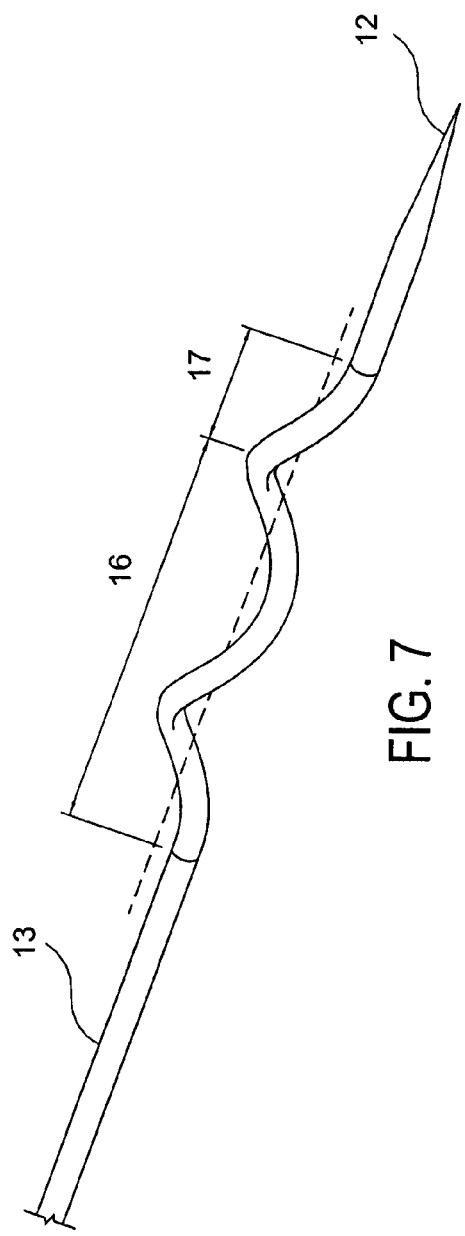

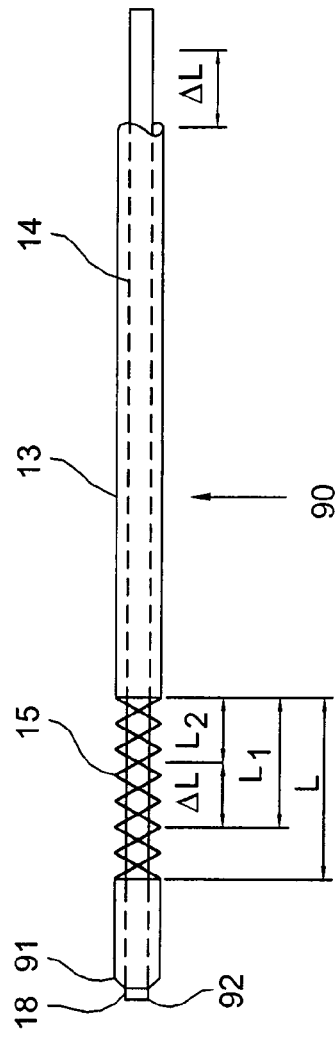
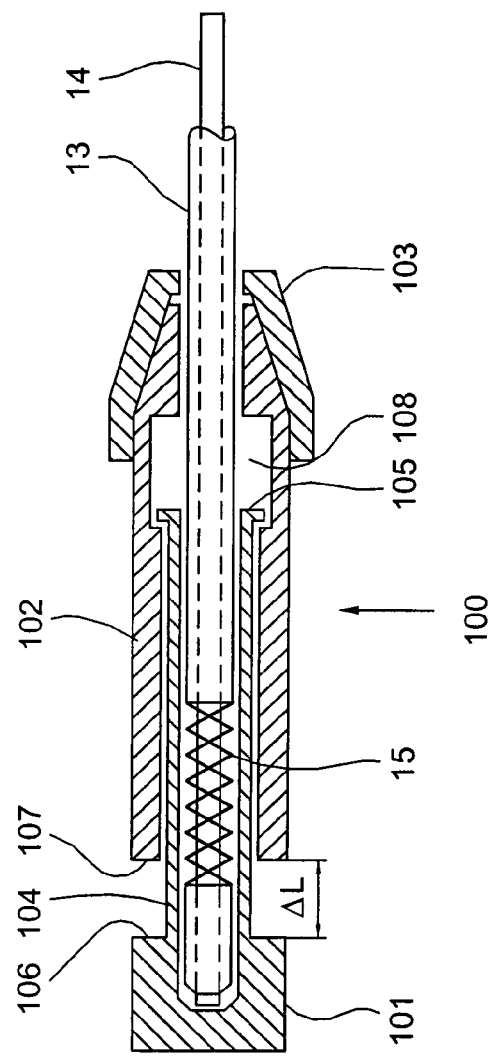

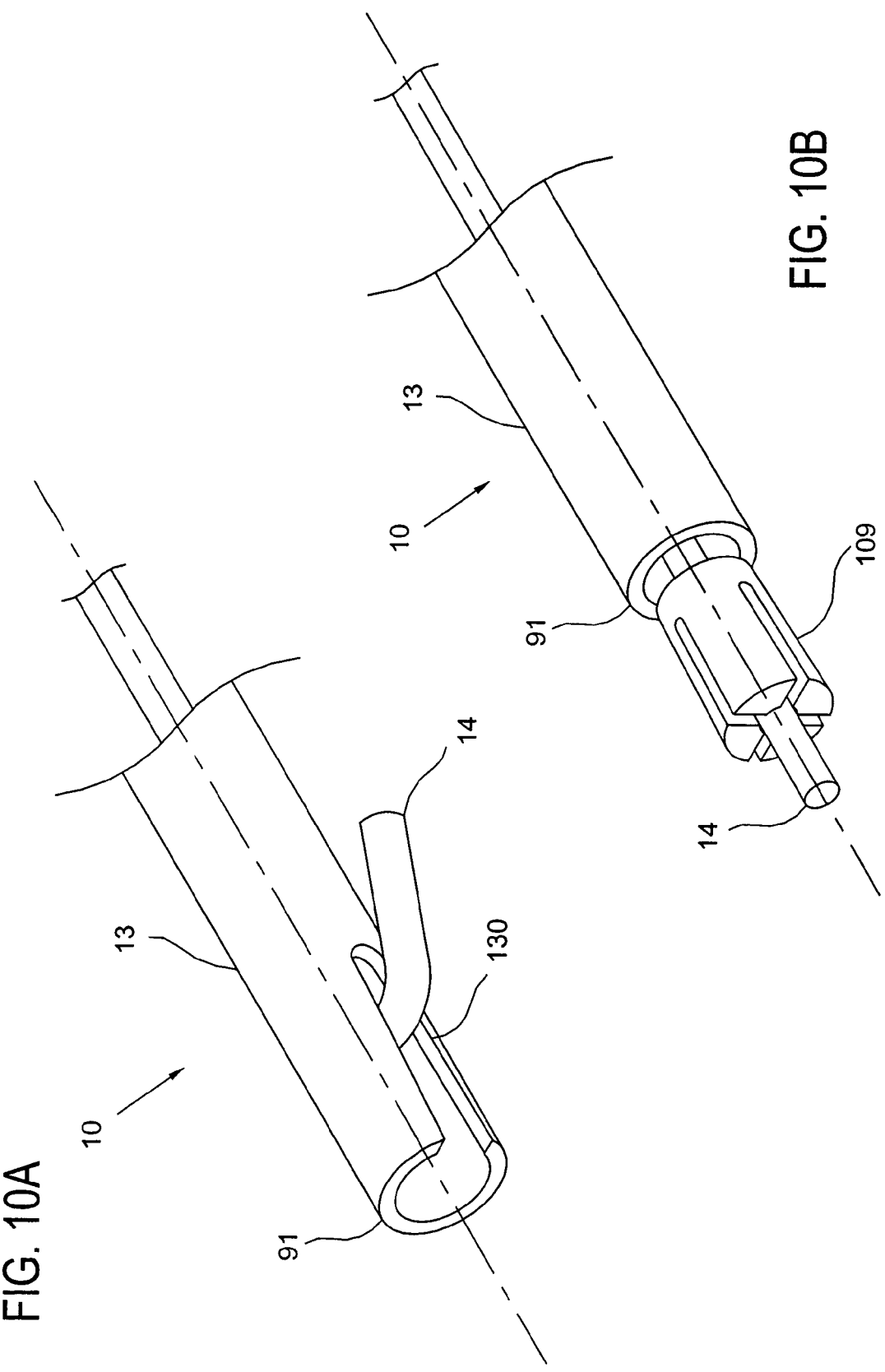

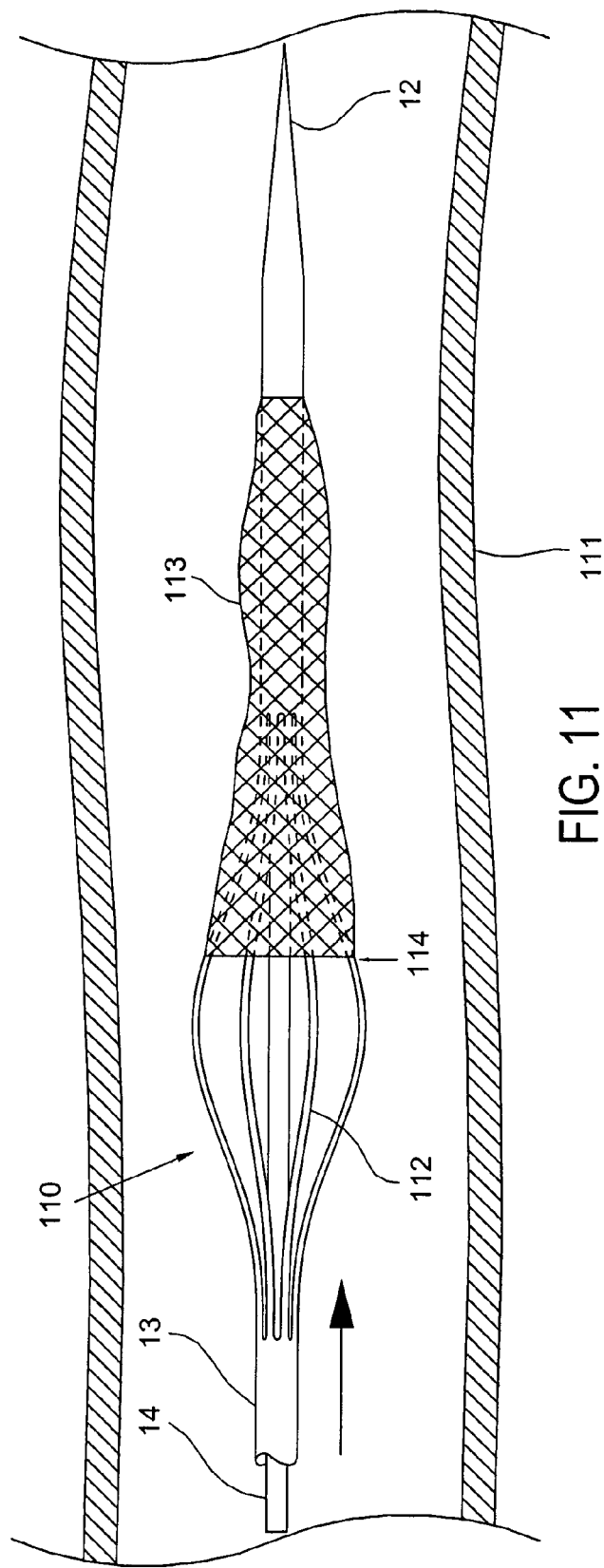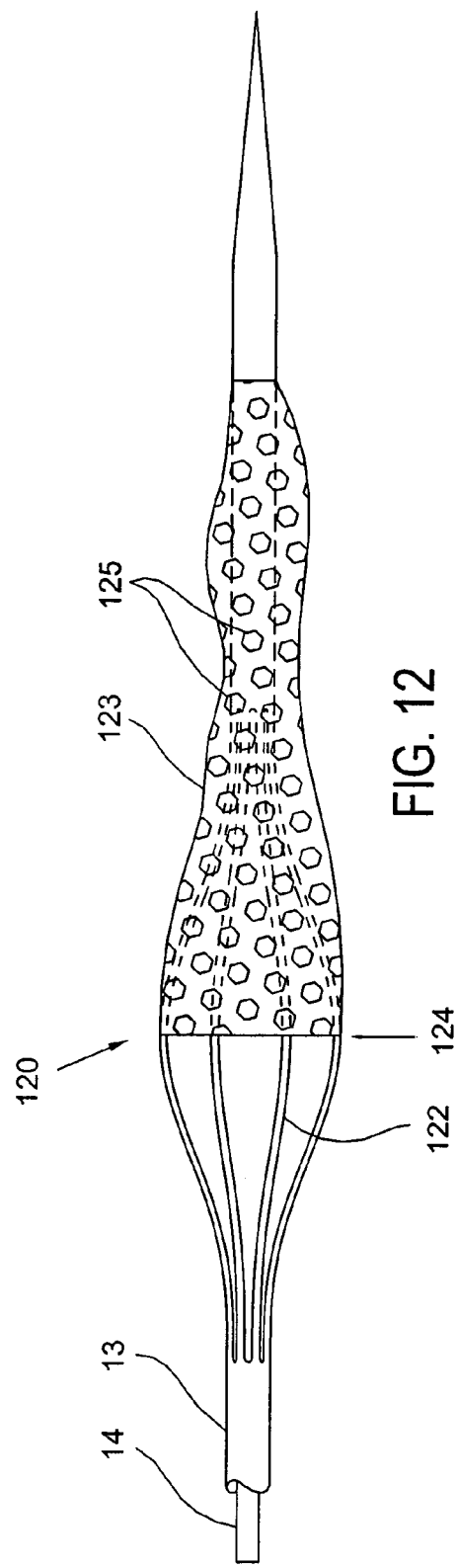

SELF-ACTIVATING ENDOLUMINAL DEVICE

This application claims the benefit of U.S. Provisional Application Ser. No. 60/514,806, filed Oct. 27, 2003.

BACKGROUND OF THE INVENTION

When a guide wire assembly is placed into a vascular, biliary, or urogenital lumen, the operator has to maintain it in place by holding the proximal end still. When a catheter or related endoluminal device is brought over the assembly, the assembly's distal end may start moving, because the relatively rigid catheter influences the geometry of the floppy guide wire, especially in tortuous arteries. The catheter will tend to straighten the guide wire assembly, thus creating a pull force on the guide wire tip, which causes an undesired movement. When the distal end of the assembly moves back in a proximal direction, it may slip out of the target artery, and if this happens, it will be necessary to pull the devices back to repeat the procedure. This is often the case if the guide wire makes a bend before the most flexible tip enters the target artery.

Previous attempts at developing a medical line anchoring system include using a simply-structured device that permits a portion of a catheter tube or similar medical article to be easily anchored to a patient, desirably without the use of tape, needles or suturing. In one exemplary device, shown and described in U.S. Pat. No. 6,447,485 to Bierman, a unitary retainer desirably includes a base connected to a cover by way of a flexible hinge. The retainer is attached to a flexible anchor pad including an adhesive bottom surface, which can be attached to the patient's skin. Such is an example of anchoring outside the body. In other approaches, elongated members that can lock themselves in place in a body site can be used. For example, in U.S. Pat. No. 6,544,262 to Fleischman discloses electrodes with an expandable tip that anchors the electrode to a body lumen or related tissue. In another method, the wire is held in place is by means of an inflatable balloon near the distal end, as shown in for example U.S. Pat. No. 6,595,989 to Schaer. Likewise, in U.S. Pat. No. 6,254,550 to McNamara et al, a preformed wire guide is shown, which can anchor itself in a side artery (for example a renal artery), because the wire has been treated to obtain a strong bend at the entrance of the side artery. At the site of this bend the wire can anchor itself, because at the given location the target artery makes a strong angle with the main access artery (aorta). Therefore the wire will hang with its bent section on the entrance of the side artery. In U.S. Pat. No. 4,884,579 to Engelson, anchoring is achieved by giving the distal section of the guide wire a less slippery surface. While such an approach increases the grip, care must be exercised during insertion when minimal friction is required, as too strong of a grip may additionally damage the vessel wall.

Guide wire assemblies with a steerable tip are well-known in the art. Some types have a shapeable tip that can be bent to a desired angle before insertion. While the angle enables the operator to find a way into side arteries, its relatively fixed nature means that once in the body, the angle can not be changed. Therefore it is better to have a remote control, where the curvature of the tip is steered by proximal actuation. In one example, hollow guide wires include a floppy tip, where a pre-bent wire can be advanced into the floppy region to change the curvature. For example, in U.S. Pat. No. 6,599,254 to Winters, a hollow guide wire with a tension wire attached to the floppy tip at an eccentric place is disclosed. If the operator pulls the tension wire relative to the guide wire, the tip will bend. The curvature can be adjusted, dependent on the pull force. In another example, U.S. Pat. No. 5,741,429 to Donadio III et al gives a hollow guide wire with a series of slots made in the tube wall at the place where more flexibility is desired. Manufacturing processes for the apparatus, including slotted hypotube, for use as a catheter, a guide wire, a catheter sheath for use with catheter introducers or a drug infusion catheter or guide wire are disclosed. The manufacturing process includes creating a pattern of slots or apertures in a flexible metallic tubular member, by processes including but not limited to, electrostatic discharge machining (EDM), chemical milling, ablation and laser cutting. These slots or apertures may be cut completely or partially through the wall of the flexible metallic tubular member. Other slotted configurations are also possible. For example, in U.S. Patent Application Publication 20030069522, a slotted medical device is described, with a plurality of pairs of slots cut into the body to make it more flexible in bending while maintaining adequate torsional stiffness.

In all cases, the actuation is controlled from the proximal end. This is done with some additional tool or actuation means, which will in general have a different geometry and typically a larger diameter than the guide wire assembly itself. Such an actuation means attached to the proximal end section makes it impossible to slide the catheter over this proximal end. Therefore, the actuation means has to be uncoupled to bring the catheter over this proximal end. This is the case for over the wire catheters as well as for rapid exchange catheters. This is disadvantageous, because in placing the catheter over the guide wire, the operator can not hold the distal section of the guide wire assembly in a fixed, anchored position.

Accordingly, there exists a need for an endoluminal device that is capable of being manipulated at a proximal end while having its distal end situated in, steered through and anchorable in a body lumen. Further, there exists a need for an endoluminal device that is in a readily-activated state to facilitate shape changes capable of producing enhanced levels of steerability and anchorability.

SUMMARY OF THE INVENTION

This need is met by the present invention, where the placement of a guide wire assembly or related medical device in a body lumen is simplified by reconfigurable features, including self-anchoring and steerable attributes. Possible embodiments include, but are not limited to, a hypotube, a catheter, steerable tip, an electrode, an angioplasty balloon, a drain, a dilator, a distal protection filter, a filter, a basket, an anchor, a floating anchor, an occlusion device, a lead, a drain, a guide wire, a catheter sheath for use with catheter introducers or a drug infusion catheter or guide wire and stylets.

The self-anchoring feature enables the assembly to have an anchor situated at an axially distal location on the assembly, while leaving radial dimensions of the assembly proximal to the anchor such that endoluminal and related treatment devices (for example, catheters) may be slid over the proximal end. By being reconfigurable, the self-anchoring and steerable features can be kept in either a deformed or undeformed shape, thereby improving maneuvering the assembly into a body lumen and proper placement in the desired location. This reconfigurable feature is achieved by varying a built-in axial force between a wire or related control element and a tubular sheath that substantially encases the control element. Connectivity between the control element and sheath, coupled with forced longitudinal movement of the control element inside the sheath, causes changes to the shape of the anchoring section and steerable section. The inherent bias resulting from the connectivity between assembly's the control element and sheath means the assembly is in its deformed state when left alone. In order to bring the device into its insertion state by changing the geometry of one or both of the steerable and anchoring sections, simple actuation at the assembly's proximal end is all that is required.

According to an aspect of the invention, a medical device for use in a body lumen is disclosed. The device includes a tubular sheath and an elongate control element. Both the sheath and the control element include proximal and distal ends. The sheath further includes at least one reconfigurable section disposed between its proximal and distal ends, and an elastic bias section. The control element (which in one particular embodiment is a wire) is sized to allow longitudinal placement thereof within the sheath, the sheath and control element fixedly attached to one another such that a tensile force is imposed by the sheath on the control element. The tensile force is sufficient to bias the medical device in a deformed first shape that can be changed by variation of the tensile force. In changing the tensile force, the medical device assumes a second shape different from the deformed first shape. In the present context, a device is considered to exist in a deformed shape when the inherent bias force causes the device to assume a shape different than the device would exhibit in a state of rest if no such force were imposed. For example, with a tension force existing between the control element and the sheath, a bend in one or both ends of the device produced by this tension would cause a (preferably elastic) deviation from a normally straight shape. In such case, the bent shape is considered deformed. Similarly, radial or related outward expansion of the sheath caused by an axial compression of the portion intermediate the connected ends would amount to a deformed shape. Contrarily, a device is considered to exist in an undeformed shape when any inherent bias forces have been overcome such that the device assumes a shape commensurate with no net forces acting upon it.

The elastic bias section is disposed proximal relative to the reconfigurable section, and is configured to vary the axial length of the sheath's reconfigurable section, thereby producing the variation of the tensile force between the sheath and the wire. The elastic bias section assists in compensating the relative movement between the control element and the sheath in the reconfigurable section by allowing relative movement of the sheath and the control element in the vicinity of the proximal end of the device. To achieve this, the elastic bas section acts as a bias spring to create an axial force necessary to keep the reconfigurable section in its deformed state. Actuation (such as by a user or operator) of the bias spring will cause a release of the axial force on the control element and so allow the spontaneous return of one or both of the anchoring and steerable sections (both discussed below) from a deformed shape to an undeformed or lesser deformed shape.

Optionally, the variation of the tensile force used to overcome the bias force may be a reduction in the tensile force. In another option, the distal end of the wire is fixedly attached to the corresponding distal end of the sheath, and the proximal end of the wire is fixedly attached to the corresponding proximal end of the sheath while the elastic bias section is in an axially compressed state. This forms a tensile force on the wire such that when left in an undisturbed state, the device has a bias tension. An additional option includes coupling a tool to at least one of the wire or the sheath to help regulate relative axial positions between the wire and the sheath. This allows changes to the built-in bias to effect transition between the first substantially deformed shape and the undeformed or lesser deformed second shape. The tool may further include markings, displays or related indicia to apprise a user of an amount of bias remaining in the elastic bias section. Similarly, the tool comprises indicia configured to apprise a user of an amount of deformation associated with the second shape. The tool comprises a connector to facilitate its removable attachment to the wire, sheath or both. In one form, the connector is a lock. In a more specific form, the lock comprises a threaded connection between the tool and the sheath.

The reconfigurable section of the sheath may be made up of numerous components. For example, it may include the aforementioned steerable section disposed adjacent the respective distal ends of the control element and the sheath. The steerable section may be configured to allow bending along at least a portion of its length. This bend defines one possible form of the deformed second shape mentioned above. These bends may be facilitated by forming at least one slot in the sheath. This slot or slots may be oriented in various directions, including axially, tangentially, circumferentially or in any angle between 0 and 90 degrees relative to the longitudinal axis of the device. In another form, the steerable section may be made up of numerous steerable regions, thereby allowing for additional insertion capability in tortuous lumens. In this case, the bends formed in each of the plurality of steerable regions can be biased (through, for example, the aforementioned slots or related places of weakening formed in the sheath) in directions independent of the remainder of the plurality of steerable regions. Another form of preferential bending can be achieved by including a coil spring in the sheath. To provide additional bias capability, a rigidity element may be placed asymmetrically in the coil spring. A similar approach can be incorporated by placing a longitudinal reinforcement along the outer surface of the sheath such that it produces an axially asymmetric rigidity.

In place of (or in addition to) the steerable section discussed above, the reconfigurable section of the sheath may include an anchoring section. This section's contribution to the device's deformed first shape corresponds to an expanded state. Contrarily, when the anchoring section is in an unexpanded state, it contributes to the device's undeformed or lesser deformed second shape. In one form, the expanded state comprises a substantially radially expanded state. In another form, the expanded state comprises a substantially helical shape. The anchoring section may include a plurality of struts with slots defined therebetween, giving the anchoring section a basket-like configuration. These struts can be oriented along a substantially axial dimension of the sheath, or can be placed in an off-axis direction. In one particular example, the anchoring section is a simple Nitinol basket, cut by means of a laser and then heat treated in its stretched, cylindrical state. When the distal and proximal ends of such a basket are pulled closer to each other by means of the internal control element under tension, the struts will bend outward, resulting in an increased basket diameter. By attaching the control element to the distal end of the basket and subsequently releasing the pulling force (such as by axially pushing on the elastic bias section at the proximal end of the device), the struts will return to their straight state, causing the basket to collapse. In another embodiment, the anchoring section may be made up of a mesh layer configured as a collapsible basket. In this way, both anchoring and filtering (discussed below) functions can be achieved by a single expandable/collapsible device disposed in the sheath. In a particular form, the wire mesh basket may be made of a self-collapsing material, such as Nitinol or related shape-memory materials.

In addition, the reconfigurable section of the sheath can be made up of both a steerable section and an anchoring section, where preferably the steerable section is disposed downstream of the anchoring section. At least one of the steerable and anchoring sections may be made elastically deformable in response to the variation of the inherent bias force.

Regardless of whether the anchoring section is provided with the steerable section or alone, it may additionally include a flexible polymer layer disposed over the struts. The polymer layer may be configured as a filter, bag or related device. For example, to be a filter, apertures or related perforations may be formed through the layer surface. Configured as a bag, the flexible polymer layer has an open proximal entrance mouth and a closed distal end. The proximal entrance mouth of the bag can be coupled to the struts at a distal location relative to a largest diameter defined by the struts in the anchoring section's expanded state. When configured as a bag, the hydraulic pressure difference inherent in a flowing bodily fluid (such as blood) can be exploited to push the device with a partially-deployed floating anchor deeper into the body lumen. For example, by having the bag be either partially or fully expanded, the pressure difference between the proximal and distal sides of the bag provides a driving force that propels the device downstream. When the bag has no apertures, the application of the fully expanded bag in the body lumen may cause the lumen to become fully occluded, which may be useful in specific applications. If a pattern of apertures is made into the layer, the floating anchor does not occlude the lumen, allowing it to be used as a filter for embolic protection. In another embodiment, the filter may be made of a wire mesh instead of a perforated polymer layer. Such a wire mesh filter may be attached directly to the anchoring section struts in a manner similar to the polymer layer. The wire mesh filter may be integrated with the anchoring section, wherein the wire mesh structure becomes expandable by the same relative axial displacement between the control element and the surrounding sheath.

The device may further include one or more endoluminal devices that can slidably fit over the sheath, at least when the sheath is in the substantially undeformed second shape. The endoluminal device can be at least any of a catheter, steerable tip, stent, filter, angioplasty balloon, drain, dilator, filter, basket, anchor, floating anchor, occlusion device, guide wire, stylet, electrode, lead, drain, catheter sheath for use with catheter introducers or a drug infusion catheter, as well as combinations of the above. Similarly, the device itself may be a catheter, steerable tip, stent, filter, angioplasty balloon, drain, dilator, filter, basket, anchor, floating anchor, occlusion device, guide wire, stylet, electrode, lead, drain, catheter sheath for use with catheter introducers or a drug infusion catheter, or combination of the above. Furthermore, materials making up the control element and sheath can be made from polymers, metals or similar structural constituents, or combinations thereof. In a particular form, the metal can be a shape-memory metal. These materials are especially valuable for applications requiring reconfigurable, bistable or related components.

According to another aspect of the invention, a guide wire assembly for use in a body lumen is disclosed. The assembly includes a tubular sheath, wire and elastic bias section to control the variation in the force between the sheath and the wire. The sheath defines a proximal end, a distal end and at least one reconfigurable section disposed intermediate the proximal and distal ends. The wire defines a proximal end and a distal end that are placed substantially adjacent to and substantially aligned with the respective ends of the sheath to facilitate a fixed attachment. As with the previous aspect, a force imposed by the sheath on the wire sufficient to bias the assembly in a substantially deformed first shape can be overcome by a variation in the force such that upon application of the variation in force, the assembly assumes a less deformed second shape different from the deformed first shape. The elastic bias section can be disposed in or otherwise formed in the sheath to effect this variation in force. In one particular form, the sheath itself can form the necessary elastic bias section, where a polymer sheath has enough longitudinal elasticity to act as a compression spring. Such a configuration simplifies the overall construction. Slots or related cut-outs could be included to facilitate an enhanced longitudinal elastic response.

Optionally, the assembly includes a tool coupled to the elastic bias section, thereby facilitating control of the variation in force between the sheath and wire. In another option, the reconfigurable section or sections comprise a steerable section disposed adjacent the distal end of the control element and the sheath. As previously described, the steerable section is bendably responsive to the variation in the force. Also as previously described, the assembly may include an anchoring section (either with or without the steerable section) expandably responsive to the variation in the force. The anchoring section may assume a substantially expanded state when the assembly is in the first shape, and an unexpanded state when the assembly is in the undeformed second shape.

According to still another aspect of the invention, a medical device with a transformable distal shape for use in a body lumen is disclosed. The device includes a hollow elongate member and an elongate control element sized to freely move longitudinally in the hollow elongate member. The hollow elongate member and the elongate control element are fixedly attached to each other at their respective proximal and distal ends. If the elongate member and control element were to be disassembled and separately measured in an undeformed state, the length of the elongate control element would be shorter than the hollow elongate member. Thus, when assembled and connected at their respective ends, the elongate member and the control element impose a bias force on each other.

Optionally, the hollow elongate member is provided with at least two sections that can be elastically deformed in a longitudinal direction. These sections include an elastic bias section located adjacent the proximal end of the elongate member, and a reconfigurable section located intermediate the proximal and distal ends of the elongate member. The reconfigurable section is cooperative with the elastic bias section such that relative movements between the elongate control element and the elongate member produce a change in shape of the reconfigurable section. As previously discussed, a biasing force is caused by stored energy in the elastic bias section. This force is sufficient to bring the reconfigurable section into a deformed shape. A removable tool can be used for length control and consequent change in shape of the reconfigurable section, where the change in shape of the reconfigurable section includes shape changes suitable for inserting into a body lumen. To allow for various shapes between a fully deformed shape and an undeformed shape, the tool cooperates with the elastic bias section to produce intermediate positions for the reconfigurable section.

As previously discussed in conjunction with other aspects of the invention, the reconfigurable section may include a plurality of steerable sections, and an expandable anchoring section responsive to changes in force between the elongate member and the control element. Each of the plurality of steerable sections may be configured to be responsive to different levels in force between the elongate member and the control element. Furthermore, they may preferentially deform into similar shapes and directions, or do so independently of one another. At least one of the plurality of steerable sections may define a pattern of slots formed in a wall of the elongate member. In addition, at least one of the plurality of steerable sections comprises an additional asymmetric reinforcing element, where the asymmetric reinforcing element can be disposed on the outer surface of the elongate member.

The anchoring section may also form a basket as previously described. The basket is made up of a plurality of struts configured to facilitate changes of shape between a first deformed shape and a second shape. A flexible polymer layer may additionally be disposed over at least a portion of the basket. This layer may be configured as a bag such that the layer defines an open proximal entrance mouth. This mouth may be located distal of the radially widest portion of the basket. The polymer bag may be used to form a pressure difference between proximal and distal sides of the bag. In one form, the bag can be used to at least partly occlude a body lumen. In another form, the polymer layer includes apertures formed in its surface. In this configuration, the bag is adapted for use as a filter for catching debris that pass through the body lumen.

The tool can be made removable from the device. This allows the reconfigurable section to remain in the body lumen even after removal of the tool. The device may further include one or more treatment devices configured to be deployed inside the body lumen over the proximal end of the elongate member. Treatment devices may include guide wires, catheters, steerable tips, stents, filters, angioplasty balloons, drain, dilators, filters, baskets, anchors, floating anchors, occlusion devices, guide wires, stylets, electrodes, leads, drains, catheter sheaths for use with catheter introducers or a drug infusion catheter, or combinations of the above. The tool is applied to control the geometry of the reconfigurable section while either or both of the device and the treatment device are moved through or positioned in the body lumen. The tool may also include a display or related indicia configured to inform an operator about an operational status of the reconfigurable section. Materials making up the elongate member may include polymers (including high-strength polymers), metal and metal with enhanced radio-opacity (including magnetic resonance imaging) features. It will be appreciated by those skilled in the art that the control element may be made from a different material than the elongate member. The length difference of the elongate member and the control element can be adjusted at or near a proximal fixation end of the device by a releasable locking means. This locking means may form part of the tool described above, or be a separate member.

According to yet another aspect of the invention, a method of inserting a medical device into a body lumen is disclosed. The device includes a tubular sheath and an elongate control element, each defining proximal and distal ends that can be coupled together. In addition, the sheath includes one or more reconfigurable sections disposed intermediate its proximal and distal ends, as well as on the elastic bias section. The elastic bias section, sheath and control element are attached to one another such that a bias force is imposed by the sheath on the control element through the elastic bias section. This bias force is sufficient to keep the device in a deformed first shape. The method includes introducing the device into the lumen and imposing a force on the device to overcome the bias force, thereby causing the medical device to assume a less deformed (or undeformed) second shape different from the deformed first shape.

In one optional form, imposing a force on the device comprises imposing a force on a proximal end of the device. As with previous aspects, a tool can be coupled to the device such that the force being imposed on the device is transmitted through the tool. One way to impose a force on the device is to remove a tensile force on the control element. In one particular option, the reconfigurable section in the sheath comprises a steerable section. This steerable section can (as previously discussed) define numerous steerable regions. One or more of these steerable regions can be made to deform in a substantially similar direction upon the imposing a force on the device to overcome the bias force. In another configuration, the steerable regions can be made to deform in a substantially different direction from the other regions. As previously discussed, the deformed first shape can comprise a bend in the one or more steerable regions of the steerable section. Moreover, at least one place of weakness can be formed in the steerable section to establish at least one preferential direction for promoting the deformed first shape. By way of example, the place of weakness can be one or more slots defined in the sheath. As previously discussed, the steerable section may comprise a coil spring placed along the sheath. This coil spring can have the same outer diameter as the sheath. In a preferred embodiment, the coil spring replaces a section of the sheath material. A rigidity element may also be employed asymmetrically in the coil spring, as in a manner similar to that previously discussed. The steerable section may also include a longitudinal reinforcement disposed asymmetrically along the outer surface of the sheath. The transitioning from a first deformed shape to a second shape may also be achieved through an anchoring section similar to that previously described. In one particular way, the amount of expansion in the anchoring section can be controlled to allow it to come in significant contact with the inner wall of the body lumen, or to a radial dimension less than that sufficient to contact an interior wall of the lumen but more than the second shape.

As before, the method may include coupling a mesh or a polymer layer to the anchoring section. This layer can form a bag, filter or related device, all as discussed above. In these forms, the layer can be used to filter a fluid through the bag, or (in the case of a partially-expanded bag) to take advantage of flowing fluid through or into the bag to facilitate downstream movement of the device. In an alternate embodiment, rather than having a wire mesh be placed over a series of expandable and collapsible struts, the anchoring section may be formed by a wire mesh configured as a basket, thereby reducing the amount of redundant structure. As with the wire mesh coupled to the struts, this wire mesh basket can be made to expand or collapse, depending on the amount of force imposed on the device. Also as before, a tool can be coupled to the proximal end of the device to effect transition between the first deformed shape and the second undeformed or lesser deformed shape of the steerable section, anchoring section or both. In addition to the basket-like shape of the anchoring section that can be formed when alternating struts and slots are used, the anchoring section may be configured as a helical shape upon the imposing of the bias force. In addition, the steerable section can be made to cooperate with the anchoring section such that both assume a helical shape upon the imposing of the bias force. The amount of change in the bias force can be made proportional to the amount of force needed to change between first and second shapes for the anchoring and steerable sections, thereby allowing them to deform or undeform in a particular order. For example, while a three Newton tensile force may be sufficient to keep the steerable section deformed, a larger force (such as a five Newton tensile force) may be required to keep the anchoring section deformed. Moreover, varying the tensile force between upper and lower limits may allow varying degrees of lesser deformation, such as a partially expanded anchoring section or a lesser amount of bend in the steerable section.

BRIEF DESCRIPTION OF THE DRAWINGS

The following detailed description of the preferred embodiments of the present invention can be best understood when read in conjunction with the following drawings, where like structure is indicated with like reference numerals and in which:

FIG. 1 shows portions of an endoluminal device in an undeformed insertion state according to an embodiment of the invention;

FIG. 2 shows a detail of a steering section of the device of FIG. 1, where a part of the steering section is deformed;

FIG. 5 shows a detail of the steering section of the device of FIG. 1, where a larger part of the steering section is deformed than in FIG. 2;

FIG. 6 shows a detail of the steering section of the device of FIG. 1, where an even larger part of the steering section is deformed than in FIG. 5;

FIG. 7 shows an embodiment of the device of FIG. 1, including a helical anchoring section in a deformed state, and steerable section in a deformed state;

FIG. 9 shows an embodiment of an elastic bias section of the device of FIG. 1 near the device's proximal end;

FIG. 10 shows a tool used to maneuver the wire and attached adjacent the proximal end of the guide wire assembly of FIG. 9;

FIG. 10A shows an alternate embodiment for a releasable connection of several parts at the proximal end of the guide wire assembly;

FIG. 10B shows yet another embodiment for a releasable connection of several parts at the proximal end of the guide wire assembly;

FIG. 11 gives another embodiment of the invention, with a floating anchor;

FIG. 12 gives still another embodiment of the invention in which the anchor section works as a filter;

FIG. 13b shows a second state where the elastic bias section is slightly compressed relative to the bias section of FIG. 13a;

DETAILED DESCRIPTION OF THE PREFERRED EMBODIMENTS

Figure 3:
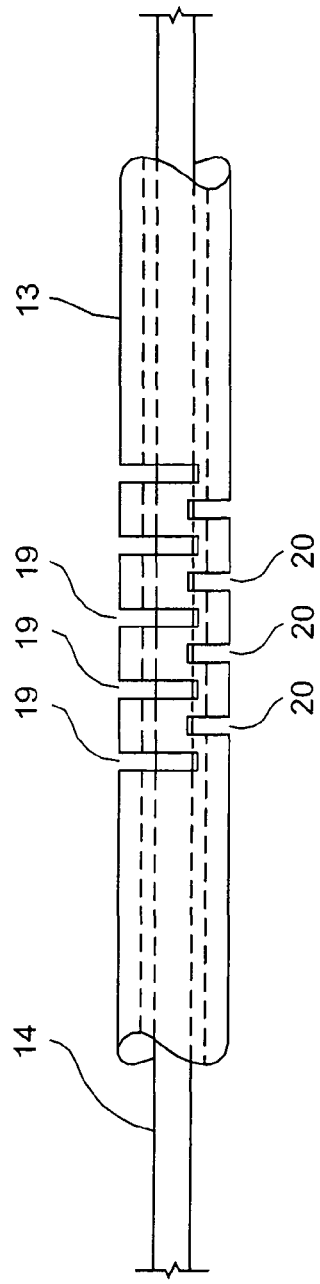
FIG. 3 shows a detail of the device of FIG. 1 with a pattern of slots disposed in its sheath.

Referring first to FIG. 1, a tubular-shaped guide wire assembly 10 is shown. While the present disclosure emphasizes a device for guide wire applications, it will be appreciated by those skilled in the art that but the same principle can be used for a range of different endoluminal applications, including catheters, steerable tips, stents, filters, angioplasty balloons, drains, dilators, filters, baskets, anchors, floating anchors, occlusion devices, guide wires, stylets, electrodes, leads, drains, catheter sheaths for use with catheter introducers or a drug infusion catheter, or related medical devices. At one end, the assembly 10 includes a proximal end 11 configured to be gripped by an operator or connected to a handle, tool or related device. The opposing distal end 12, configured to be inserted into a body lumen (not shown), terminates in a tip. Guide wire assembly 10 includes a sheath 13 that can encase wire 14 that acts as a control element for steering and anchoring purposes.

In general, it is advantageous if the distal end 12 of the guide wire assembly 10 is relatively compliant or floppy, while the majority of the length should be kink resistant, pushable, bendable and able to transmit torsional forces from the proximal to distal ends 11, 12 in order to maneuver the assembly 10 accurately. The sheath 13 can be chosen from any wire or hypotube material suitable for guide wire or catheter applications. One specifically suitable material is superelastic Nitinol, a nickel-titanium alloy with shape-memory properties that is well-known for its flexibility, pushability, biocompatibility and kink resistance. In one configuration, the majority of the length of the tube may made of metal while an anchoring section (discussed in more detail below) may be made from a relatively soft and flexible material that easily deforms when the wire 14 being moved causes an axial compression in the sheath 13. The wire 14 can be made of a high strength yet flexible polymer. If improved visibility for MRI or related radio-opacity is needed, additional markers of materials like gold, platinum, silver, tungsten, iridium or the like may be used at specific locations on either the wire 14 or sheath 13. Other material choices include metals and related materials for improved strength, stiffness or visibility for MRI or radio-opacity.

Sheath 13 is made up of numerous distinct sections, including elastic bias section 15, located near the proximal end 11, long intermediate section 10a, anchoring section 16 and steerable section 17. While intermediate section 10a does not possess significant longitudinal elasticity, elastic bias section 15 and anchoring and steerable sections 16, 17 are made in such a way that they respond with a considerable shape change to the forces that are generated between sheath 13 and control wire 14. Steerable section 17 includes a floppy tip 17a and connector 17b, the latter used to attach a distal end of the wire 14 to the wall of sheath 13. Floppy tip 17a may be relatively short, and may even be integrated with steerable section 17, in which case connector 17b is placed at the most distal end 12. An important attribute associated with the anchoring section 16 and steerable section 17 is that the relative movement between the wire 14 and the sheath 13 produce a shape change that is sufficient to change the size, shape or both of the assembly 10, depending on the insertion and anchoring needs. Such shape changes are especially valuable if the surrounding tissue has a cylindrical shape, as non-axisymmetric or varying-diameter lumens tend to form their own anchoring points. In addition, the difficulty of traversing sharply-bent lumens is reduced if the distal end 12 can be made to approximate the lumen's change in shape. Accordingly, the steerable section 17 can form one or more curves. Both the steerable section 17 and the anchoring section 16 can be activated by axially moving wire 14 relative to sheath 13. This can be effected by an attachable tool (discussed later), placed at or near the proximal end 11 of guide wire assembly 10 to interface with both ends of biasing section 15. Once the biasing tension force has been applied between wire 14 and sheath 13, the proximal ends of wire 14 and sheath 13 can be connected permanently (as shown later in FIG. 9) or in a releasable way (as shown later in FIGS. 10A and 10B).

Steerable Features

Referring next to FIGS. 2, 5 and 6, embodiments depicting a guide wire assembly 10 with relative movement of wire 14 inside sheath 13 to effect variations in the steerable section 17 are shown. In one form, there can be a pull force applied to the proximal end 18 of wire 14. This pull force will cause a change of shape of steerable section 17, where floppy tip 17a extends to the distal end 12 of guide wire assembly 10. This shape change can be made to depend on the amount of force applied. In this way, a gradient in shape change is achieved in order to combine steerability upon insertion with anchoring after insertion.

FIG. 2 shows a detail of steerable section 17 of guide wire assembly 10 adjacent its distal end 12 in bent form, with regions X, Y and Z defining distinct steerable portions of section 17 which have been made more flexible than the relatively rigid intermediate section 10A. As such, the steerable section 17 can be tailored such that distal end 12 flexes in a controlled way in a preferred direction. For example, slots (described below in conjunction with FIG. 3), cut-outs and related places of weakness may be formed in region X to facilitate preferential bending. The slots can be made in such a way that region X flexes at the lowest force, region Y at a higher force and region Z at a still higher force. It will be apparent to those skilled in the art that the relative position of regions X, Y and Z can be chosen arbitrarily, and that the number of such regions is dependent on the type of use. Accordingly, such regions may be overlapping or blended in a different way. Similarly, the functions of floppiness, steerability and anchoring may be mixed within such regions. In the present figure, only region X is deformed, because only a small proximal pull force is applied to wire 14; with increasingly larger pull forces, regions Y and Z would also become deformed, such as described next.

Referring with particularity to FIG. 5, when the pull force is increased relative to that of FIG. 2, the flexure caused in region X is followed by an additional flexure of region Y. Depending on how the slots or related deformation-enhancing elements are formed, the curvature of region Y can be in the same direction as for region X, or in the opposite direction (as shown), or in a different plane (not shown). Referring with particularity to FIG. 6, the pulling force is further increased, causing region Z to change shape as well. As with region X discussed above, regions Y and Z may include slots or similar places of weakness built into sheath 13. This gradual change of the guide wire assembly 10 geometry at regions X, Y and Z enables more precise control of the distal section 12. A display (not shown) may be used to provide indicia of the force applied or the relative movement between sheath 13 and the wire 14. In one form, the display may be an electronic device, while in another, it may be made up of graduated markings disposed between the sheath 13 and wire 14. This enables the operator to keep the guide wire assembly 10 straight upon insertion, steer the distal end 12 to maneuver it into side lumens and then finally anchor it in the desired lumen location in order to proceed with using a catheter or related device.

Figure 4:
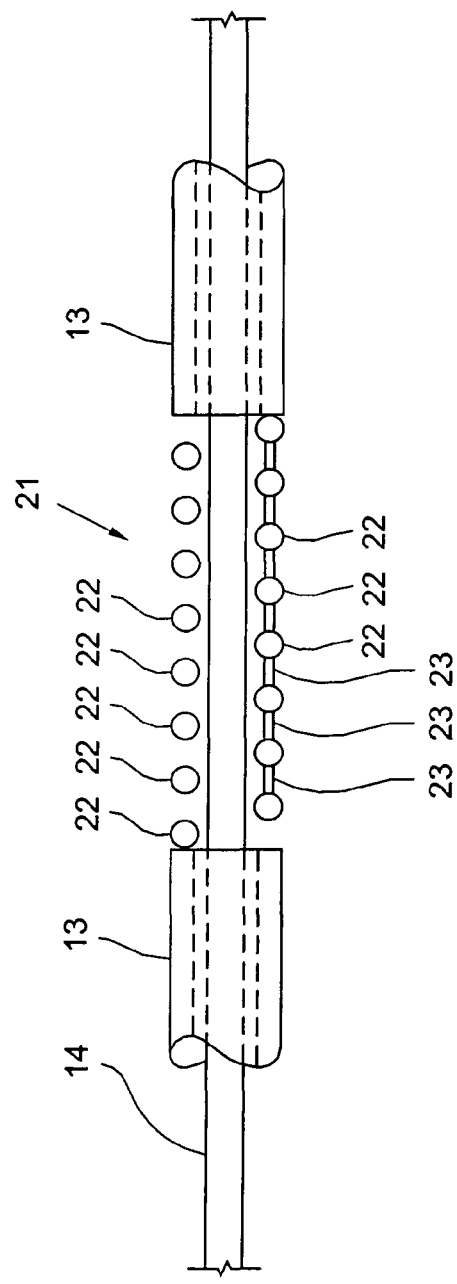
FIG. 4 gives an alternative detail of the device of FIG. 3, showing a separate flexible part.

Referring next to FIGS. 3 and 4, features promoting the curvature of steerable section 17 shown in FIGS. 2, 5 and 6 are shown. Referring with particularity to FIG. 3, examples of an asymmetric pattern of deep slots 19 and shallow slots 20 formed in sheath 13 promotes the preferential deformation of the guide wire assembly 10 previously discussed and shown. The slot patterns 19, 20 in the distal end 12 of guide wire assembly 10 not only enable steerability, but also makes that portion of the sheath 13 more flexible. This promotes insertability of the assembly 10 into a desired location within the body lumen by elastically deforming a section of the wall of sheath 13. For example, deep slots 19 are located such that upon pulling wire 14, the shortening of region X will be larger at the concave side (where deep slots 19 are located) than at the convex side, where shorter slots 20 may be located. As previously mentioned, similar slots are also made in region Y and Z, although the slot pattern may be different than in region X, as these regions need more force to bend.

Referring with particularity to FIG. 4, while the choice of making slots 19, 20 in the sheath 13 is one way to promote the axial deformation of regions X, Y and Z to achieve the shape change shown in FIGS. 2, 5 and 6 upon pulling on wire 14, it will be appreciated by those skilled in the art that other ways may also be employed. For example, flexible coil spring 21 with an asymmetric rigidity disposed between adjacent coils may be formed in sheath 13 to effect similar bending. For example, a gap between adjacent coils 22 is left open on one side; this gap is variable upon spring compression. Opposite the gaps, rigidity element 23 is placed between successive coils. In one form, rigidity element 23 is a polymer, glue or related material that resists change of lengths between adjacent coils. Other materials may be used to create a flexible section similar to coil spring 21 to effect guide wire assembly 10 bending if a pull force is applied to wire 14. This includes the use of polymer tubing where, for example, an eccentric lumen holds the wire 14. Another possibility is the use of an eccentric reinforcement (not shown), acting as a spine, which is embedded in the wall of the polymer tubing. In such case, both ends of the flexible section are connected to the remainder of the sheath 13. This connection between this flexible section and the sheath 13 may be achieved by any known technique, including the use of welding, crimping, brazing, gluing or embedding in a surrounding cover material.

Anchoring Features

Operation of the anchoring section 16 causes changes in guide wire assembly 10 diameter by means of local radially outward expansion in anchoring section 16. As with the aforementioned steerable section 17, discussed in conjunction with FIGS. 2, 5 and 6 above, a pulling bias force is applied between wire 14 and sheath 13. By varying this force (such as through an operator pushing on wire 14) to cause a relative movement between wire 14 and sheath 13, a corresponding change of shape of anchoring section 16 can be effected. As with shape changes in steerable section 17 made possible with pulling on wire 14, changes in shape of anchoring section 16 can be made to depend on the amount of force applied. In this way, a gradient in shape change is achieved in order to combine steerability upon insertion with anchoring after insertion. The anchoring features of the anchoring section 16 can be augmented by inherent anchoring features produced in steerable section 17. For example, steerable segments X, Y and Z of section 17 can, when they are in their bent state, increase the friction with the lumen wall, thereby producing an additional anchoring function.

Figure 8:
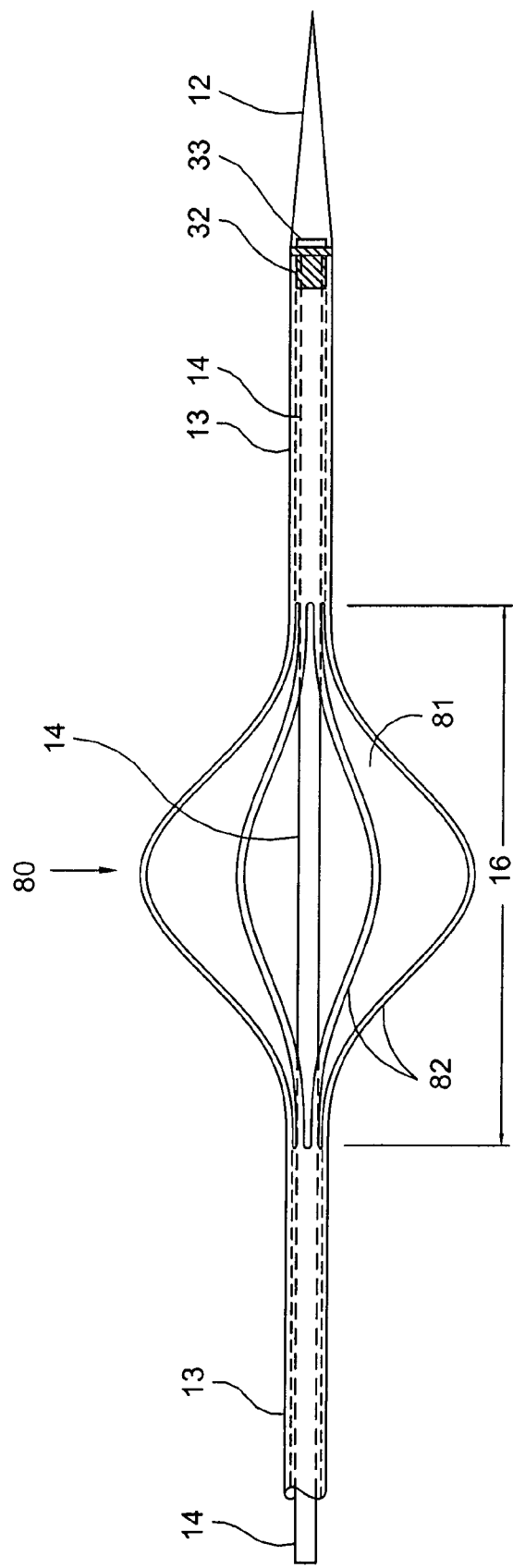
FIG. 8 shows an alternate embodiment of the anchoring section in a deformed state.

Referring next to FIG. 8 in conjunction with FIG. 1, the anchoring section 16 is shown in the shape of an expandable basket 80, made by forming longitudinal slots 81 in the wall of sheath 13 to define struts 82 therebetween. Connector 32 is used in a manner similar to that of the connection point 17b depicted in FIG. 1, where the distal end of the wire 14 is connected to a crimped end 33 or related attachment means. As before, distal end 12 may be tapered and similarly attached. The rigidity of the struts 82 is such that they will have the tendency to straighten out along the axial dimension of guide wire assembly 10 if a force sufficient to overcome the bias force is imposed on wire 14. This is made possible by the larger exertion of the sheath 13 relative to wire 14 to define a first, retracted radial dimension that coincides with an insertion state of the guide wire assembly 10, such as shown in FIG. 1. In operation, the pulling on wire 14 inherent in the bias force brings the distal end 12 toward proximal end 11, and because of the attachment of wire 14 to sheath 13, basket 80 shortens as the struts 82 gradually bend outward, causing sheath 13 to assume an expanded radial dimension shown in FIG. 8. Preferably, the expanded radial dimension corresponds to the inner dimension of the lumen wall so that basket 80 tightly anchors the sheath 13 to this lumen. Although the struts 82 and slots 81 are shown arranged in a generally longitudinal (i.e., axial) pattern, it will be appreciated by those skilled in the art that they need not be so oriented, but may be made in different angles and patterns to tailor the behavior of the anchoring section 16 to a particular lumen need.

While the anchoring section 16 may be formed in the wall of sheath 13 as shown in order to keep the design simple and monolithic, it can in another form be made from a different component and built in the guide wire assembly, thereby allowing the use of potentially different materials. One example of a non-monolithic embodiment would be the use of a separate wire mesh basket (not shown) for anchoring section 16, attached to a sheath 13 formed from a more conventional steel tube. In this way, the wire mesh basket could be incorporated that performs the same duties as the struts 82. An additional benefit (as described later in conjunction with FIG. 12) is that the wire mesh basket, by having the same collapsible and expandable features of the strut version of anchoring section 16 is that it can also perform filtering functions without the need for a separate layer attached to struts. In one form, such a basket could be made from Nitinol or related shape-memory materials.

One way of producing such a device would be the use of a steel tube with for example an outer diameter of 0.35 mm, which is glued inside the tube of which the Nitinol basket is made. The inside diameter of the basket tube could be 0.40 mm and the outside diameter 0.45 to 0.50 mm. As such, the wire 14 slides without friction through the steel tube. Furthermore, the anchoring section 16 may have different geometries than those shown in FIG. 8. For example, the struts 82 could be longer and placed partly parallel to the longitudinal axis, or the struts 82 could be placed in a zigzag pattern (not shown) to improve the radial strength or wall apposition of the basket. Such additional struts may also be used to connect extra devices to the surface of the basket. Besides the anchoring function (which increases longitudinal friction), the radial force of the basket may also be used for different applications. For example, it can work as a dilator, for example for applying a force to a lesion or to post-dilate a region in the lumen that has been stented.

Operation of the Guide Wire Assembly

FIG. 9 highlights the portion of guide wire assembly 10 between proximal end 11 and elastic bias section 15, the latter including unobtrusive flexibility features useful in enabling the assembly's steering and anchoring functions. Length L in elastic bias section 15 represents the unloaded length of the elastic bias section 15. The variable length features are made possible by either connecting a separate tubular spring with length L in elastic bias section 15 to the sheath 13, or providing sheath 13 over a length L with a pattern of slots (not shown, but similar to slots 19, 20 of FIG. 3) that create the same effect. In either approach, the small radial dimensions ensure that the flexible, elastic features fit within the footprint of the sheath 13. In the latter approach, sheath 13 is still of unitary (i.e., one-piece) construction, thereby preserving its inherent torque and buckling resistance while providing an increase in axial elasticity. Instead of making slots in elastic bias section 15, the use of a sheath 13 with a polymer section, which has enough longitudinal elasticity, can also enable a compression spring-like bias.

As previously mentioned, guide wire assembly 10 is preloaded to keep the wire 14 in a state of tension. To achieve this, the proximal end 18 of wire 14 is attached to the corresponding end of sheath 13 while elastic bias section 15 of sheath 13 is compressed to length L1. Attachment is effected by permanently crimping a separate attachment element 92 onto the proximal end 18 of wire 14, or by crimping together the respective ends of sheath 13 and wire 14. Alternative attachment schemes are also available, including gluing, welding or related bonding. After attachment, elastic bias section (presently shown in the form of a compressed spring) 15 attempts to return to length L. In so doing, the bias force created by the compressed spring 15 produces a tension load in wire 14 that exceeds the force needed to collapse the anchoring section 16 relative to the shape shown in FIG. 8. Thus, the fixed relationship between the wire 14 and sheath 13 at distal end 12 of guide wire assembly 10, in conjunction with the fixed relationship between the wire 14 and sheath 13 by attachment element 92 at proximal end 18 of guide wire assembly 10 and the bias force caused by the compressed spring 15 described above, keeps the wire 14 under constant tension as long as the guide wire assembly 10 is not manipulated by external forces. As a consequence, the guide wire assembly 10 remains in its expanded radial dimension of FIG. 8 during this period of no external forces. Moreover, both the steerable section 17 and the anchoring section 16 are active, meaning that without application of an external force, such as from an operator, they are in their respective bent and expanded states. Upon application of an external compression force (such as by an operator) to spring 15, the steerable and the anchoring sections 17, 16 can assume their straight and non-expanded form shown in FIG. 1. In addition, the operator can slide a catheter or other endoluminal prosthetic devices as previously discussed over at least portions of the guide wire assembly 10 while the assembly is in its expanded radial dimension, knowing that it has reached the desired location in the body and that it holds its achieved position there.

In operation, if the elastic bias section 15 is further compressed until it reaches length L2, the tension force in wire 14 will drop to zero and the distal sections 16 and 17 will return to their unbiased state such that the guide wire assembly 10 has a relatively straight, unexpanded and smooth shape, as shown in FIG. 1. Gradual control of the distal state of guide wire assembly 10 takes place in control range ΔL that is equal to the difference between the lengths L1 and L2.

Referring next to FIG. 10, tool 100 can be used to improve the functionality of the guide wire assembly 10. With tool 100, it will be easier to activate the steering and anchoring functions in gradual steps, thereby providing enhanced control of the geometry of the guide wire assembly 10, including intermediate positions between the fully unactivated (retracted) state and the fully activated (expanded) state. In addition to preventing the buckling of elastic bias section 15 or the inadvertent deployment of the anchoring or steerable sections 16, 17, tool 100 can be used to provide smooth length control and an accurate position read-out. This read-out, which may be in the form of a display as previously discussed, can give information about the status of the reconfigurable section, which is especially beneficial when the operator wants to know about intermediate states of deployment or actuation of the anchoring or steerable sections 16, 17. In one form, the tool 100 resembles a tubular member that may be mounted over the entire proximal end of sheath 13. As shown in the figure, tool 100 is made from two separate pieces that can be made to vary along their axial dimension relative to one another over length ΔL. Proximal part 101 is connected to and holds the proximal end 11 of sheath 13, while distal part 102 of tool 100 is clamped on the surface of sheath 13 distally of elastic bias section 15 with a screw lock 103 made from a thread or snap connection. Proximal part 101 further includes an elongate cylindrical section 104 onto which distal part 102 may telescopically fit. The distal end of cylindrical section 104 forms a flange 105 to allow a snap-fit engagement with distal part 102. Flange 105 can move freely through an enlarged diameter chamber 108 that is formed in distal part 102. In such a construction, parts 101 and 102 can be slid over the proximal end 11 of guide wire assembly 10 until the operator feels that the end of the internal cavity formed in proximal part 101 touches the proximal end 11 of the guide wire assembly 10 as shown. The operator then tightens lock 103 (such as by screwing) to distal part 102. This ensures the operator that length ΔL is available for controlling the shape of the remote steerable and anchoring sections 17, 16 respectively. One way this can be achieved is by visually checking a gap formed between complementary surfaces 106 and 107 of respective proximal and distal parts 101 and 102. The operator may further adjust this gap to a smaller length to make the guide wire assembly 10 coincide with a slightly bent or expanded shape when it is desired to have the steering section 17 be angled for better maneuverability or the anchoring section 16 to be in an intermediate state of deployment. This is achieved as follows: the operator can control a part of ΔL by first pushing surfaces 106 and 107 closer to each other before tightening lock 103. Upon tightening by lock 103, the steerable and anchoring sections 17, 16 will not return completely to their straight unbiased state when the operator pushes surfaces 106 and 107 to each other. For example, the anchoring section 16 may collapse while the steerable section 17 is still in its bent state, commensurate with the amount of force placed on wire 14. By unlocking lock 103, the operator can simply remove tool 100 to enable subsequent placement of the catheter or related device over the proximal end 11 of the guide wire assembly 10.

By having the wire 14 be pre-loaded in a manner similar to that previously discussed in conjunction with FIG. 9, the guide wire assembly 10 can be kept in an activated state even though an operator is not manipulating the wire 14 relative to the sheath 13. When the operator pushes on proximal part 101, the guide wire assembly 10 becomes deactivated. Tool 100 may be provided with thread, allowing precise axial distance control by relative rotation between the proximal and distal parts 101, 102. Proximal locking made possible with lock 103 allows the operator to maintain the shape of one or both of the steerable and anchoring sections 17, 16 when the guide wire assembly 10 is left alone. The operator may permit some free axial play between the proximal end 11 of guide wire assembly 10 and proximal part 101. In an alternate form, proximal part 101 and cylindrical section 104 are not one single part, but separated, so that the length of cylindrical section 104 can be adjusted by means of a threaded connection (not shown) between cylindrical section 104 and the internal cavity of proximal part 101.

A well known alternative for tool 100, which may be used for the adjustment of ΔL, is the mechanism commonly found in ball point pens, where a simple axial movement of part 101 automatically causes a locking of the displacement ΔL, thus bringing the device into an undeformed state. By pressing another time on part 101, it will unlock again and the device returns immediately to its deformed state. Such ball point pen actuators are also made in different embodiments, for example with axial translation caused by rotating the proximal knob. Such devices can very well be used to move part 101 relative to part 102 in a reliable, predictable and simple way.

Insertion of the guide wire assembly 10 into a body lumen normally takes place while gap ΔL between complementary surfaces 106 and 107 abut one another. As soon as the guide wire assembly 10 is in place, lock 103 is released and the tool of combined proximal and distal parts 101, 102 is removed from the guide wire. At that moment the anchoring section 16 will be active; moreover, a catheter or related medical device may be applied over the guide wire assembly 10 and inserted into the patient. Catheters or related devices can be slid over the guide wire assembly 10 until it reaches the expanded anchoring section 16; to advance it farther, the guide wire assembly 10 will need to be connected back into its insertion (i.e., unexpanded) state. This would also be the case once the guide wire assembly 10 has to be removed through the catheter.

Referring next to FIGS. 10A and 10B, alternative ways of locking the assembly 10 are shown. In these variants, a releasable proximal lock for the control wire 14 replaces the permanent stop 92 used in FIG. 9, which due to its fixed attachment, can not be modified by the operator once attached. Referring with particularity to FIG. 10A, a detail of the proximal end 91 of a guide wire assembly 10 shows how actuation can also be achieved by a long control element, such as a flexible wire 14 (made, for example, of a high strength polymer). If no pull force is applied proximally, the assembly 10 will be in the insertion state. At the proximal end, the sheath 13 may have a short tapered slit 130 in its wall, in which the operator can lock the control element. This can be done by first applying the necessary axial force for actuation of the guide wire assembly 10 and than bending the wire 14 sideward until it locks itself in the slit 130. The friction will then hold the wire 14 stationary locked in the tube wall.

Referring with particularity to FIG. 10B, yet another embodiment of the removable lock is shown, where the wire 14 may include a tapered sliding stop 109 that fits tight inside the proximal end 91 of the sheath 13 while deforming elastically. This elastic deformation will then increase the friction between the sliding stop 109 and the wire 14, enough to lock the assembly 10 into its anchored or steered position. The friction can also be lowered again by pulling the tapered stop 109 a little bit out of the sheath 13, so that readjustment is possible. The sliding stop 109 may also be provided with longitudinal slots to make it easier to deform elastically.

Referring next to FIG. 7, another embodiment of anchoring section 16 and steerable section 17 of sheath 13 is shown. Close to distal end 12, a short steerable section 17 is attached to helical anchoring section 16. Helical section 16 is shaped to have a smooth elastic contact with the surrounding lumen or related tissue. In this instance, the pattern of slots (not shown)

will be configured to produce a differently bending pattern from the one shown in FIGS. 2, 5 and 6. Techniques to produce the patterned slots, such as by laser cutting similar to those used for making stents and related endoluminal prosthetic devices, may be employed. Other methods, such as mechanical cutting with fine blades, may also be used. While the above-mentioned cutting techniques are especially well known for metals, it will be appreciated by those skilled in the art that the guide wire assembly 10 of this invention may be made of different materials, like polymers, or even combinations of different materials entailing known, concomitant production techniques as needed.

Referring next to FIG. 11, an alternate embodiment anchoring section 110 is disclosed. In the anchoring section 16 of the previous embodiments, blood or related body fluid can flow freely around, resulting in a very small resulting force caused by the pressure difference over the anchoring section 16. In some cases, especially in very thin arteries, it may be difficult to maneuver the guide wire assembly 10 to a remote place; in such cases, it can be advantageous to use the blood flow to pull the guide wire assembly 10 into the target location. By placing a thin cone-shaped polymer skin 113 onto the struts forming basket 112 anchoring section 110, a parachute-like bag is formed. Through the use of a tool (such as tool 100 shown in FIG. 10), the basket 112 can be deployed to a partially-deployed state in a manner similar to that previously discussed. The forces associated with fluid flow (represented by the arrow in the figure) in the lumen (such as an artery) 111 can be used if the anchoring section 110 is brought into this partially-deployed state where, although not touching the inner wall of lumen 111, has enough of an increased radial dimension perpendicular to the major axis to take advantage of the force produced by the fluid flow.

The cone-shaped polymer skin 113 is attached distally to the struts at attachment sites 114 close or at the place where the diameter of the basket 112 is greatest. The fluid that gets trapped in the bag formed by basket 112 and polymer skin 113 will pull the guide wire assembly downstream as it fills with blood or related fluid. The advantage is that this reduces or eliminates the need for the operator to apply proximal pushing on the guide wire assembly. The other features, including the aforementioned steerability and anchoring, can still be used. Upon anchoring of guide wire assembly, the expanded polymer skin 113 may completely occlude the target artery, while in an alternate embodiment of the invention, the geometry of the basket 112 and polymer skin 113 may be chosen so that perfusion always remains around the polymer skin 113, even when the anchoring section 110 is deployed. Both variants are intended as embodiments of the invention, with the perfusion variant discussed in more detail next.

In FIG. 12, a variant on the design of FIG. 11 is given, where a parachute-like bag can still be used, but in which it is combined with a filtering function. Now the anchoring section 120 is provided with an expandable basket 122, distally covered with a filter bag 123, which is attached to the basket near the attachment points 124. The difference with the embodiment of FIG. 11 is that the filter bag 123 is now provided with a series of small patterned holes 125 to give the filter bag 123 its filtering functions. Such holes 125 have multiple functions. First, they prevent the full occlusion of fluid flow as mentioned above. Further, they can be used to filter emboli and related particulate matter with a predetermined minimum diameter. This is especially interesting if the guide wire assembly is used in combination with a catheter for angioplasty, stenting or related procedures. The geometry and quantity of holes 125 depend on the size of the particles that have to be caught, as well as on the desirable level of flow that needs to continue when the filter bag 123 is deployed. The available surface area in the filter bag 123 for making such holes further depends on the geometry of the filter bag 123; for example, if bag 123 has a long conical shape as shown, it will allow the presence of a large number of holes 125. In another embodiment, the filter may be made of a wire mesh instead of a perforated polymer layer. Such a wire mesh filter may be attached directly to the anchoring section struts in a manner similar to the polymer layer. Alternatively, a wire mesh filter may be integrated with the anchoring section, wherein the wire mesh structure becomes expandable by the same relative axial displacement between the control element and the surrounding sheath.

Figure 9A:
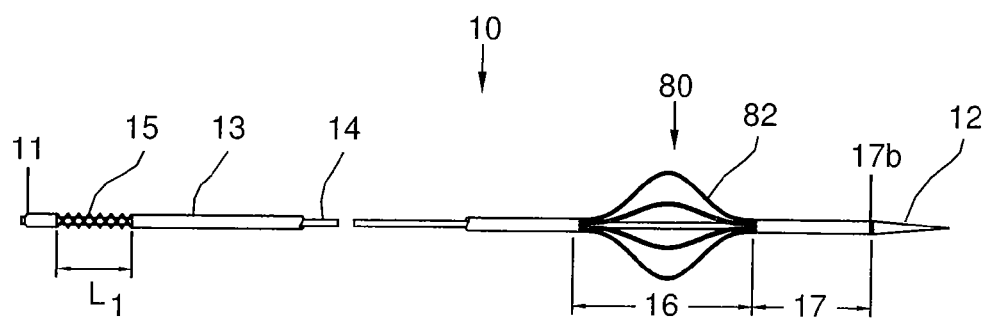
FIG. 9a shows the proximal section of FIG. 9 and the distal section of FIG. 8 assembled together.

The following drawings will elucidate the construction of the assembly 10, clearly showing the corresponding points of attachment of the control wire 14 and the surrounding sheath 13. Referring with particularity to FIG. 9a, the proximal end 11 of FIG. 9 and the distal end 12 of FIG. 8 are shown assembled together. For clarity, the long mid-section of control wire 14 and sheath 13 are left out of the drawing in order to enable visualization of the relevant parts at the opposing ends. Referring with particularity to FIG. 9a in conjunction with FIG. 1, the distal end 12 of the device has a floppy tip 17a, which extends distally beyond the connector 17b of steerable section 17, where such steerability features are shown in FIGS. 2, 5 and 6. In the free state depicted in FIG. 9a, the assembly 10 is self-activated such that the length of sheath 13, if measured between the corresponding points of attachment, is equal to the length of the control wire 14, while the bias spring 15 has length L1, as shown in FIG. 9. In addition, the basket 80 of anchoring section 16 is in the expanded state, such as shown in FIG. 8. Control wire 14 is connected to sheath 13 at the proximal end 91 of guide wire assembly 10 at the permanent stop 92 in FIG. 9, and at connector 32 that is situated in the crimped end 33 in FIG. 8.

Figure 9B:
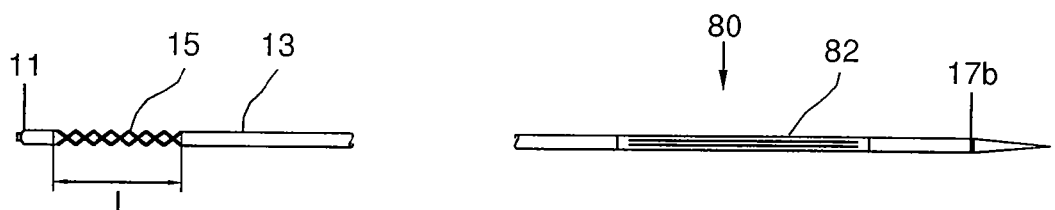
FIG. 9b shows the outer element of the assembly of FIG. 9a with the wire removed.
Figure 9C:
FIG. 9c shows the wire of the assembly of FIG. 9a with the outer element removed.
Figure 13A:
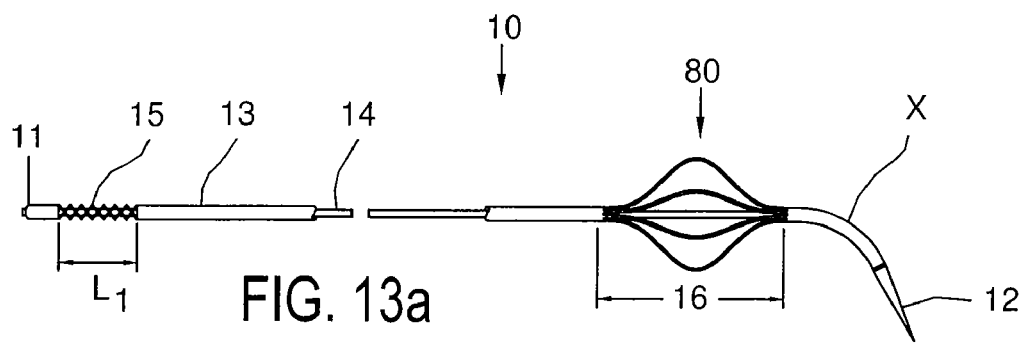
FIG. 13a shows a first state of a device with a combination of the anchoring section of FIG. 8 and the steerable section of FIGS. 1 and 2, where the elastic bias section is compressed into a preloaded state.
Figure 13B:
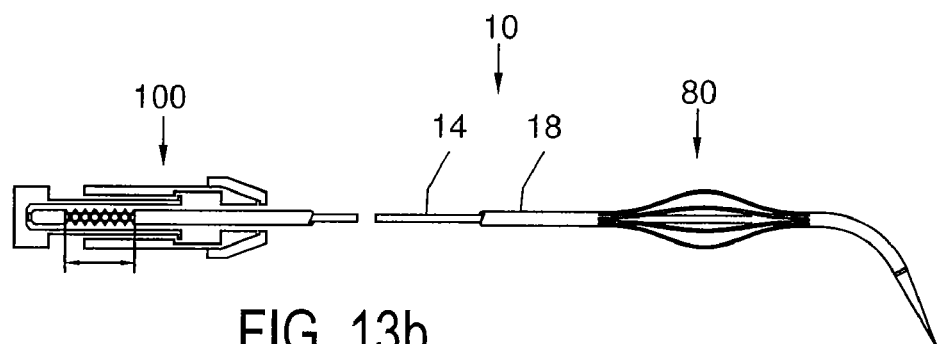
Figure 13C:
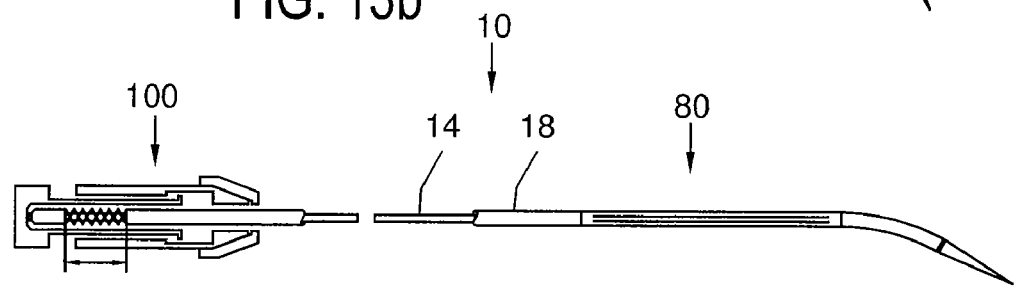
FIG. 13c shows a third state where the elastic bias section is slightly compressed relative to the bias section of FIG. 13b.
Figure 13D:
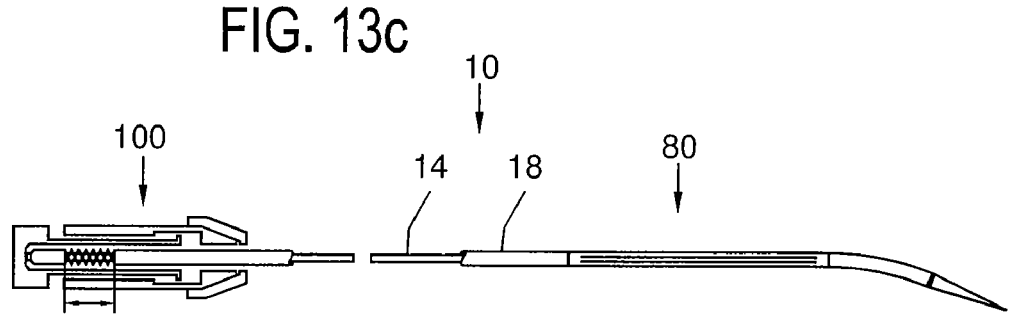
FIG. 13d shows a fourth state where the elastic bias section is slightly compressed relative to the bias section of FIG. 13c.
Figure 13E:
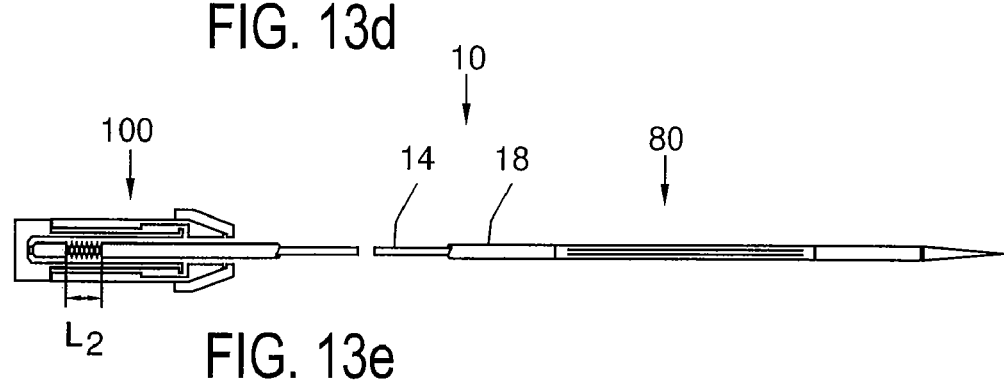
FIG. 13e shows a fifth state where the elastic bias section is slightly compressed relative to the bias section of FIG. 13d.

Referring with particularity to FIGS. 9b and 9c, sheath 13 (FIG. 9b) is shown detached from wire 14 (FIG. 9c). In such detached state, the sheath 13 would become longer for two reasons. First is the unloading of the proximal bias spring 15, from length L1 into length L, both of which are depicted in FIGS. 9 and 9a, and both of which allow the overall length from the proximal and distal ends 11, 12 to extend, as shown by the increased length at the proximal side in FIG. 9b relative to FIG. 9a. Second, there is the elongation of the basket section 80 at the distal side as it stretches out axially from its radially expanded shape in FIG. 9a to its radially contracted shape in FIG. 9b. This latter feature is due, as previously discussed, to guide wire assembly 10 being pre-loaded to keep the wire 14 in a state of tension through attachment to the corresponding end of sheath 13. After attachment, elastic bias section (presently shown in the form of a compressed spring) 15 attempts to return to length L. In so doing, the bias force created by the compressed spring 15 produces a tension load in wire 14 that exceeds the force needed to expand the anchoring section 16 relative to the shape shown in FIG. 9b. Thus, but for the tendency of the wire 14 to pull the proximal and distal ends of sheath 13 toward one another, sheath 13 assumes a longer length (as shown in FIG. 9b relative to FIG. 9a).

FIG. 9c shows the control wire 14 removed from the guide wire assembly 10 of FIGS. 1, 8 and 9. While the length of wire 14 may be subject to minor variations upon loading and unloading, such length change is very small relative to the length changes of sheath 13 that are produced by length changes in spring 15 and basket 80. By preloading the bias spring 15 and the expandable basket 80 to the state as shown in FIG. 9a, it becomes possible to line up the ends of the elongated element 13 of FIG. 9b with the corresponding ends of wire 14 of FIG. 9c, whereafter the step of attachment of sheath and wire 13 and 14 at the respective points takes place by one of the methods previously mentioned, such as gluing, welding, crimping or the like.

Referring next to FIG. 13 in conjunction with FIGS. 2 through 6, bendable region X of steerable section 17 is shown immediately distal of basket section 80. Such an embodiment gives a combination of an anchoring section and a steerable tip to the guide wire assembly 10, as previously discussed. FIGS. 13a through 13e show the several intermediate stages of activation of such an assembly 10, with FIGS. 13b through 13e showing with more particularity the tool 100 of FIG. 10 attached over the proximal end 11 in order to partially or entirely steer, collapse and deploy the assembly 10. Tension force changes in the control wire 14 will bend the tip at relatively low force (as shown in FIGS. 13c and 13d), while increasing the force will finally also cause expansion of the anchoring section 16 (as shown in FIGS. 13b and finally 13a). Thus, the two extreme states of the device are the self-activated position of FIG. 13a and the fully stretched tip and collapsed basket section of FIG. 13e, where the latter is the state used for initial insertion of the assembly 10. Removal or other disconnection of the tool 100 from the assembly 10 will cause the assembly 10 to revert into the state depicted in FIG. 13a, as spring 15 will change from fully compressed length L2 of FIG. 13e into length L1 of FIG. 13a, moving the tip and basket section accordingly such that the assembly 10 can act as a self-activating distal protection filter with steerable tip for enhanced navigation, amongst others.

It will be appreciated by those skilled in the art having regard to this disclosure that other modifications of this invention beyond these embodiments specifically described herein may be made without departing from the spirit of the invention. Accordingly, such modifications are considered within the scope of the invention as limited solely by the appended claims.

What is claimed is:

1. A medical device for use in a body lumen, said device comprising:
    a tubular sheath comprising:
        a proximal end;
        a distal end opposite said proximal end;
        at least one reconfigurable section disposed intermediate said proximal and distal ends; and
        an elastic bias section disposed proximal relative to said reconfigurable section, said elastic bias section configured to vary the axial length of said reconfigurable section; and
    an elongate control element defining a proximal end and a distal end, said control element sized to allow longitudinal placement thereof within said sheath, said sheath and control element fixedly attached to one another at substantially opposing ends thereof such that a tensile force is imposed by said sheath on said control element through said fixed attachment, said tensile force sufficient to bias said reconfigurable section in an expanded first shape that can be overcome by imparting an external force on said sheath through said elastic bias section such that said medical device assumes a second shape different from said first shape.

2. The device of claim 1, wherein said control element comprises a wire.

3. The device of claim 2, wherein the distal end of said wire is fixedly attached to the corresponding distal end of said sheath, and the proximal end of said wire is fixedly attached to the corresponding proximal end of said sheath while said elastic bias section is in an axially compressed state, thereby effecting said tensile force upon said wire.

4. The device of claim 3, further comprising a tool coupled to at least one of said wire or said sheath, said tool configured to regulate relative axial positions between said wire and said sheath and thereby effect transition between said first shape and said second shape.

5. The device of claim 4, wherein said tool comprises indicia configured to apprise a user of an amount of bias extant in said elastic bias section.

6. The device of claim 4, wherein said tool comprises indicia configured to apprise a user of an amount of deformation extant in said second shape.

7. The device of claim 4, wherein said tool comprises a connector to facilitate removable attachment of said tool to said at least one of said wire or said sheath.

8. The device of claim 7, wherein said connector comprises a lock.

9. The device of claim 8, wherein said lock comprises a threaded connection between said tool and said sheath.

10. The device of claim 1, where said reconfigurable section comprises a steerable section disposed adjacent said distal end of said sheath.

11. The device of claim 10, wherein said first shape comprises a bend in at least a portion of said steerable section.

12. The device of claim 11, wherein said steerable section comprises a plurality of steerable regions within said reconfigurable section.

13. The device of claim 12, wherein said bends formed in each of said plurality of steerable regions are biased in directions independent of the remainder of said plurality of steerable regions.

14. The device of claim 12, wherein said first shape comprises a bend in a plurality of said plurality of steerable regions.

15. The device of claim 10, wherein said steerable section defines at least one slot formed in said sheath.

16. The device of claim 15, wherein said at least one slot defines at least one of an axial, tangential or circumferential slot.

17. The device of claim 16, wherein angles defining said at least one slot comprise a plurality of different angles, all oriented between 0 and 90 degrees with the longitudinal axis of said sheath.

18. The device of claim 10, wherein said steerable section comprises a coil spring disposed in said sheath.

19. The device of claim 18, further comprising a rigidity element disposed asymmetrically in said coil spring to define a preferential direction of said bend.

20. The device of claim 10, wherein said steerable section further comprises a longitudinal reinforcement disposed asymmetrically along the outer surface of said sheath.

21. The device of claim 1, where said reconfigurable section of said sheath comprises an anchoring section configured to assume an expanded state when said medical device is in said first shape and an unexpanded or less expanded state when said medical device is in said second shape.

22. The device of claim 21, whereupon said expanded state comprises a substantially radially expanded state.

23. The device of claim 21, whereupon said expanded state comprises a substantially helical shape.

24. The device of claim 21, wherein said anchoring section comprises a mesh layer configured as a collapsible basket.

25. The device of claim 21, wherein said anchoring section comprises a plurality of struts with slots defined therebetween.

26. The device of claim 25, wherein said plurality of struts are oriented along a substantially axial dimension of said sheath.

27. The device of claim 25, wherein said anchoring section comprises a wire mesh disposed over said struts.

28. The device of claim 25, wherein said anchoring section further comprises a flexible layer disposed over said struts.

29. The device of claim 28, wherein said flexible layer comprises a polymer material.

30. The device of claim 29, wherein said polymer layer is configured as a filter, said filter defining a plurality of perforations within its surface.

31. The device of claim 29, wherein said flexible polymer layer is configured as a bag with an open proximal entrance mouth and a closed distal end.

32. The device of claim 31, wherein the proximal entrance mouth of said bag is coupled to said struts at a distal location relative to a largest diameter defined by said struts in said expanded state.

33. The device of claim 1, where said reconfigurable section of said sheath comprises a steerable section and an anchoring section, said steerable section distally disposed relative to said anchoring section.

34. The device of claim 33, wherein at least one of said steerable and anchoring sections is elastically deformable in response to said variation of said tensile force.

35. The device of claim 1, further comprising an endoluminal device configured to slidably fit over said sheath.

36. The device of claim 35, wherein said endoluminal device is selected from the group consisting of a catheter, steerable tip, stent, filter, angioplasty balloon, drain, dilator, filter, basket, anchor, floating anchor, occlusion device, guide wire, stylet, electrode, lead, drain, catheter sheath for use with catheter introducers or a drug infusion catheter, and combinations thereof.

37. The device of claim 1, wherein said device is selected from the group consisting of a catheter, steerable tip, stent, filter, angioplasty balloon, drain, dilator, filter, basket, anchor, floating anchor, occlusion device, guide wire, stylet, electrode, lead, drain, catheter sheath for use with catheter introducers or a drug infusion catheter, and combinations thereof.

38. The device of claim 1, wherein materials making up said control element are selected from the group consisting of polymers, metals and combinations thereof.

39. The device of claim 38, wherein said metal is a shape-memory metal.

40. The device of claim 1, wherein materials making up said sheath are selected from the group consisting of polymers, metals and combinations thereof.

41. The device of claim 40, wherein at least a portion of said reconfigurable section comprises a shape-memory metal.

42. The device of claim 1, wherein said imparted external force comprises a reduction in said tensile force.

43. The device of claim 1, wherein said second shape is a substantially undeformed shape.

44. The device of claim 1, wherein said second shape is a partially deformed shape.

45. A guide wire assembly for use in a body lumen, said assembly comprising:
a tubular sheath defining a proximal end, a distal end and at least one reconfigurable section disposed intermediate said proximal and distal ends;
a wire defining a proximal end and a distal end, said wire and said sheath fixedly attached to one another at substantially opposing ends thereof such that a tensile force is imposed by said sheath on said wire through said fixed attachment, said tensile force sufficient to bias said reconfigurable section in an expanded first shape; and
an elastic bias section cooperative with said sheath and configured such that upon application of a variation in said tensile force through movement of said elastic bias section relative to said sheath, said reconfigurable section assumes a second shape that is less expanded than said first shape.

46. The assembly of claim 45, further comprising a tool coupled to said elastic bias section to control said variation in said force between said sheath and said wire.

47. The assembly of claim 45, wherein said at least one reconfigurable section comprises a steerable section disposed adjacent said distal end of said assembly, said steerable section bendably responsive to said variation in said force.

48. The assembly of claim 47, wherein said at least one reconfigurable section further comprises an anchoring section expandably responsive to said variation in said force.

49. The assembly of claim 45, wherein said at least one reconfigurable section comprises an anchoring section expandably responsive to said variation in said force.

50. The assembly of claim 49, wherein said anchoring section is configured to assume a substantially expanded state when said assembly is in said first shape, and a reduction in said expanded state when said assembly is in said second shape.

51. The assembly of claim 50, wherein said reduction in said expanded state comprises an unexpanded state.

52. The assembly of claim 45, wherein said elastic bias section is formed in said sheath.

53. A medical device comprising:
a hollow elongate member defining at least one reconfigurable section therein;
an elongate control element sized to fit longitudinally in said hollow elongate member, wherein said hollow elongate member and said elongate control element are fixedly attached to each other at respective proximal ends and distal ends such that a state of tension exists between said elongate control element and said hollow elongate member; and
an elastic bias member coupled to said hollow elongate member between said proximal end and said at least one reconfigurable section such that absent any external force being imparted to said device, said bias member causes said state of tension to be overcome in said device to place said at least one reconfigurable section into an expanded state that is different from an insertion state.

54. The device of claim 53, wherein said reconfigurable section is located intermediate said proximal and distal ends of said elongate member and cooperative with said elastic bias section such that relative movements between said elongate control element and said elongate member produce a change in shape of said reconfigurable section.

55. The device of claim 54, further comprising a removable tool for length control and consequent change in shape of said reconfigurable section.

56. The device of claim 55, wherein said change in shape of said reconfigurable section comprises a change into said insertion state that is suitable for inserting into and removable from a body lumen.

57. The device of claim 55, wherein the tool cooperates with said elastic bias section to produce intermediate positions for said reconfigurable section, said intermediate positions defining reconfigurable section configurations between said deformed expanded state and said insertion state.

58. The device of claim 55, whereupon removal of said tool, said reconfigurable section is configured to remain in said body lumen.

59. The device of claim 58, further comprising a treatment device configured to be deployed inside said body lumen over said proximal end of said elongate member while said reconfigurable section remains in said body lumen.

60. The device of claim 59, wherein said treatment device is selected from the group consisting of a catheter, stent, filter, angioplasty balloon, drain, dilator, filter, basket, anchor, floating anchor, occlusion device, guide wire, stylet, electrode, lead, drain, catheter sheath for use with catheter introducers or a drug infusion catheter, and combinations thereof.

61. The device of claim 60, wherein said tool is applied to control the geometry of said reconfigurable section while either or both of said device and said treatment device are moved through or positioned in said body lumen.

62. The device of claim 60, wherein said tool comprises a display configured to inform an operator about an operational status of said reconfigurable section.

63. The device of claim 54, wherein said reconfigurable section comprises:
a plurality of steerable sections, each of said plurality of steerable sections responsive to different levels in force between said elongate member and said control element; and
an expandable anchoring section responsive to changes in said state of tension between said elongate member and said control element.

64. The device of claim 63, wherein at least one of said plurality of steerable sections defines a pattern of slots formed in a wall of said elongate member.

65. The device of claim 63, wherein at least one of said plurality of steerable sections comprises an additional asymmetric reinforcing element.

66. The device of claim 65, wherein said asymmetric reinforcing element is disposed on the outer surface of said elongate member.

67. The device of claim 63, wherein said anchoring section comprises:
a basket comprising a plurality of struts configured to facilitate changes of shape between a first deformed shape and a second shape; and
a flexible polymer layer disposed over at least a portion of said basket, said layer defining an open proximal entrance mouth.

68. The device of claim 67, wherein said proximal entrance mouth is located distal of a radially widest portion of said basket.

69. The device of claim 68, wherein said polymer layer is configured as a bag, said bag configured to form a pressure difference between proximal and distal sides of said bag.

70. The device of claim 69, wherein said bag is used to at least partly occlude a body lumen.

71. The device of claim 67, wherein said polymer layer defines apertures in a surface thereof.

72. The device of claim 71, wherein said polymer layer is configured as a bag coupled to said anchoring section, said bag adapted for use as a filter for catching debris that pass through said body lumen.

73. The device of claim 53, wherein materials making up said hollow elongate member and said elongate control element are selected from the group consisting of polymers, metals, metals with enhanced radio-opacity features and combinations thereof.

74. The device of claim 73, wherein said elongate control element may be made from a different material than said hollow elongate member.

75. The medical device of claim 53, wherein the length difference of said hollow elongate member and said elongate control element can be adjusted at or near a proximal fixation end of said device by a releasable locking means.

* * * * *